US00PP12468P2

(12) United States Plant Patent
Olesen et al.

(10) Patent No.: US PP12,468 P2
(45) Date of Patent: Mar. 19, 2002

(54) CLIMBER ROSE VARIETY 'POULTIKA'

(76) Inventors: L. Pernille Olesen; Mogens Olesen, both of Hillerodvejen 49, Fredensborg (DK), DK-3480

( * ) Notice: Subject to any disclaimer, the term of this patent is extended or adjusted under 35 U.S.C. 154(b) by 0 days.

(21) Appl. No.: 09/276,891

(22) Filed: Mar. 25, 1999

(51) Int. Cl.[7] ..... A01H 5/00
(52) U.S. Cl. ..... Plt./114
(58) Field of Search ..... Plt./114, 109

(56) References Cited

PUBLICATIONS

CFIA "Applications Accepted for Filing" *Plant Varieties Journal* Jul. 1998 No. 28 Canada.
Poulsen Roser Pacific "Plant Breeders Rights Application Form" Submitted Mar. 11, 1998 Canada.
Research Center for Cultivar Testing "Decision" Feb. 22, 1999. Poland.
Community Plant Variety Office "Certificate On The Grant of Community Plant Variety Rights" Aug. 3, 1998 European Union.
Community Plant Variety Office "Chapter 4: Decisions" Oct. 15, 1998 European Union.
UPOV–ROM GTITM Computer Database 2000/06, Dec. 8, 2000, GTI Jouve Retrieval Software, citation for 'Poultika'.*

* cited by examiner

*Primary Examiner*—Bruce R. Campell
*Assistant Examiner*—June Hwu

(57) ABSTRACT

A new garden rose plant which has abundant, pink flowers and attractive foliage. This new and distinct variety has shown to be uniform and stable in the resulting generations from asexual propagation.

2 Drawing Sheets

SUMMARY OF THE INVENTION

The present invention constitutes a new and distinct variety of garden rose plant which originated from a controlled crossing between an unnamed seedling (non-patented) and 'Kordes Brilliant' (non-patented). The two parents were crossed and the resulting seeds were planted in a controlled environment. The new variety is named 'POULtika'.

The new rose may be distinguished from its seed parent, an unnamed seedling, by the following combination of characteristics:

1. The habit of the seed parent is a compact shrub; whereas, 'POULtika' is a climbing rose.

2. The petalage of the seed parent is semi-double; whereas, 'POULtika' blooms are double;

The new variety may be distinguished from its pollen parent, 'Kordes Brilliant' created by the same inventors, by the following combination of characteristics:

1. The flower color of the pollen parent is orange-red, while 'POULtika's' flowers are light pink;

2. The foliage of the pollen parent is medium green, compared to 'POULtika's' dark green foliage.

The objective of the hybridization of this rose variety for nursery and garden use was to create a new and distinct variety with unique qualities, such as:

1. Uniform and abundant flowers;

2. Vigorous growth;

3. Disease resistance;

4. Large cupped flower form.

This combination of qualities is not present in previously available commercial cultivars of this type and distinguishes 'POULtika' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULtika' was selected in spring 1988 by the inventors as a single plant from the progeny of the aforementioned hybridization.

Asexual reproduction of 'POULtika' by traditional budding was first done by L. Pernille and Mogens N. Olesen in August, 1988. This initial and other subsequent propagations conducted in controlled environments have demonstrated that the characteristics of 'POULtika' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'POULtika'. Specifically illustrated in Sheet 1:

1. Stem showing branching and the attachment of leaves, buds, and peduncles;

2. Flower bud, partially opened bud, and open bloom;

3. Flower petals, detached;

4. Sepals, receptacle, and pedicel;

5. Flowering stem as well as a bare stem exhibiting thorns;

6. Leaves.

DETAILED DESCRIPTION OF THE VARIETY

The following is a description of 'POULtika', as observed in its outdoor growth in a field nursery in Jackson County, Oregon. Observations were conducted during September, 1998, on an 18 month old plant. Color references are made using The Royal Horticultural Society (London, England) Colour Chart, 1995, except where common terms of color are used.

For a comparison, several physical characteristics of the rose variety 'POULclimb', a climbing rose variety from the same inventors described and illustrated in U.S. Plant Pat. No. 10,639 and issued on Oct. 13, 1998 are compared to 'POULtika' in Chart 1.

CHART 1

| | 'POULtika' | 'POULclimb' |
|---|---|---|
| Size of open bloom. | 60–70 mm. | 75–90 mm. |
| Color of open bloom. | Red-Purple Group 65C–65D. | Striped, cream white with flecks of Red Purple Group 64D–65D. |
| Petalage. | Double, 35–40 petals | 10–15 petals. |

Parents:

*Seed parent.*—Unnamed seedling.

*Pollen parent.*—'Kordes Brilliant'.

Classification: Climber.

*Botanical.*—*Rosa hybrida.*

*Commercial.*—Climber.

FLOWER AND FLOWER BUD

Blooming habit: Nearly continuous.

Flower bud:

*Size.*—Upon opening, 30 mm–40 mm in length from base of receptacle to end of bud.

*Bud form.*—Pointed ovoid.

*Bud color.*—As sepals unfold, Red-Purple Group 65A–65D. At ¼ opening, top portion of the bud is Red-Purple Group 65B. The middle to lower portions are Red-Purple 62D, Basal area of petals visible are White Group 155C.

*Sepals.*—Upper side: Green Group 144A. Lower side: Green Group 144A. Shape: cirrose at apex, with a flat base where they join with the receptacle. Moderate foliaceous appendages on three of the five sepals. Surfaces of sepals lightly pubescent. No stipitate glands were observed on the margins of the sepals.

*Size.*—45–50 mm average length and 10–12 mm average width.

*Receptacle.*—Surface: Smooth. Shape: Funnel shaped. Size: Medium. 7 mm (h)×8 mm (w). Color: Green Group 144A.

*Peduncle.*—Surface: Smooth. Length: 30–35 mm average length. Color: Green Group 144B. Some peduncle have a light intonation of Greyed-Red Group 179C. Strength: Strong.

*Borne.*—Multiple buds per stem. Arrangement: Corymb. Generally with 6–10 buds per flowering stem.

Flower bloom:

*Fragrance.*—Light.

*Duration.*—As a cut flower 4 to 5 days. The blooms have a duration on the plant of 4 to 6 days. Petals clean reasonably well.

*Size.*—Average flower diameter is 60–70 mm when open.

*Form.*—Shape of flower when viewed from the side: Upon opening, upper part: Flattened convex. Upon opening, lower part: Flattened convex. Open flower, upper part: Flattened convex. Open flower, lower part: Flattened convex.

*Petalage.*—Double, with an average range of 35–40 petals under normal conditions with 5–8 petaloids.

Color:

*Upon opening, petals.*—Petals: Upper Surface: Red-Purple Group 65B–65C. Red-Purple Group 65B at margins; middle and basal zones are Red-Purple Group 65C and 65D, respectively. Reverse Side: Red-Purple Group 65B. Petal color is lighter in basal area; White Group 155C. Some petals with variegation of White Group 155C in the center of petal.

*Upon opening, basal petal spots.*—Petals: Outer Side: White Group 155C. Inner Side: White Group 155C.

*After opening, petals.*—Petals: Upper Surface: Red-Purple Group 65C–65D. Petal color stronger in marginal zone, diminishing to White Group 155C at basal zone. Reverse Side: Red-Purple Group 65B–65C. Petal color stronger in marginal zone, diminishing to White Group 155C at basal zone.

*After opening, basal petal spots.*—Petals: Outer Side: White Group 155C. Inner Side: White Group 155C.

General tonality: On open flower Red-Purple Group 65B–65C. No change in the general tonality at the end of the 3rd day. Afterwards, general tonality is Red-Purple Group 65C–65D.

Petals:

*Petal reflex.*—Petals reflex slightly.

*Petal edge.*—Entire.

*Shape.*—Rounded obovate.

*Petaloids.*—5–8. Petaloids are small relative to petals. Thin and velvety, colored Red-Purple Group 65B on the outer side, Red-Purple Group 73A on the inner side.

*Texture.*—Very thick, velvety texture.

*Arrangement.*—Imbricated.

Reproductive organs:

*Pollen.*—Color: Yellow Group 13B. Quantity: Average.

*Anthers.*—Size: 3–4 mm. Color: Yellow Group 11B. Quantity: 20–25. Pistils: 20–25 pistils per inflorescence.

*Filaments.*—Color: Green-White Group 157C.

*Stigmas.*—Generally superior in location to anthers. Color: Yellow-Green Group 145D.

*Styles.*—Color: Green-White Group 157A. Other intonations: Below stigma, intonations of Red-Purple Group 66C. Length: 12–17 mm.

*Stamens.*—Color: Green-White Group 157C. Length: 10–15 mm.

*Hips.*—None observed.

PLANT

Plant growth: Vigorous canes climbing to 280 cm.

Stems:

*Color.*—Young wood: Yellow-Green Group 144C. Older wood: Yellow-Green Group 144B.

*Thorns.*—Incidence: 12–17 per 10 cm of stem. Young wood: Average length is 7 mm and color is Greyed-Orange Group 173B. Older wood: Average length is 8–10 mm and color is Greyed-Orange Group 177B. Shape: Concave.

*Surface.*—Young wood: Smooth. Older wood: Smooth.

Plant foliage: Normal number of leaflets on leaves located halfway up stem: 5 to 7 leaflets.

*Leaf size.*—Medium to large. 140–150 mm (l)×90–100 mm (w).

*Quantity.*—Average to abundant.

*Color.*—Upper Leaf Surface: Green Group 137A. Lower Leaf Surface: Green Group 138B–138C. Juvenile foliage: Green Group 147A–147B. Anthocyanin: Location: Upper leaflet margins, lower leaf surfaces, petioles, rachis, stipules, stems, and peduncles. Color: Greyed-Red Group 179A.

Plant leaves and leaflets:

*Stipules.*—Size: 10 mm–15 mm. Color: Green Group 143B. Stipitate glands: Present on margins.

*Petiole.*—Length: 20 mm–25 mm. Color: Green Group 143B. Underneath: Smooth. with a limited number of small prickles.

*Margins.*—Limited stipitate glands and fine white hairs present on upper surface.

*Rachis.*—Color: Green Group 137B–137C. Underneath: Smooth. with a limited number of small prickles. Margins: Limited stipitate glands and fine white hairs present on upper surface.

*Leaflet.*—Edge: Serrated. Shape: Broadly ovate. The leaflet's apex is acuminate. The leaflet's base is rounded. Arrangement: The leaflets are arranged in an odd-pinnate formation. Venation: The leaflets are veined in a reticulate pattern. Texture: Upper side of leaflet is thick and matte. Lower side of leaflet is thick and matte.

Disease resistance: Above average resistance to mildew, black spot, and Botrytis under normal growing conditions in Jackson County, Oreg.

Cold hardiness: 'POULtika' has been found to be cold hardy in Fredensborg, Denmark and Jackson County, Oreg.

We claim:

1. A new and distinct variety of rose plant of the climbing class, substantially as herein illustrated and described as a distinct and novel rose variety due to its abundant, light pink flowers, vigorous growth, disease resistance, and extended period of bloom.

* * * * *

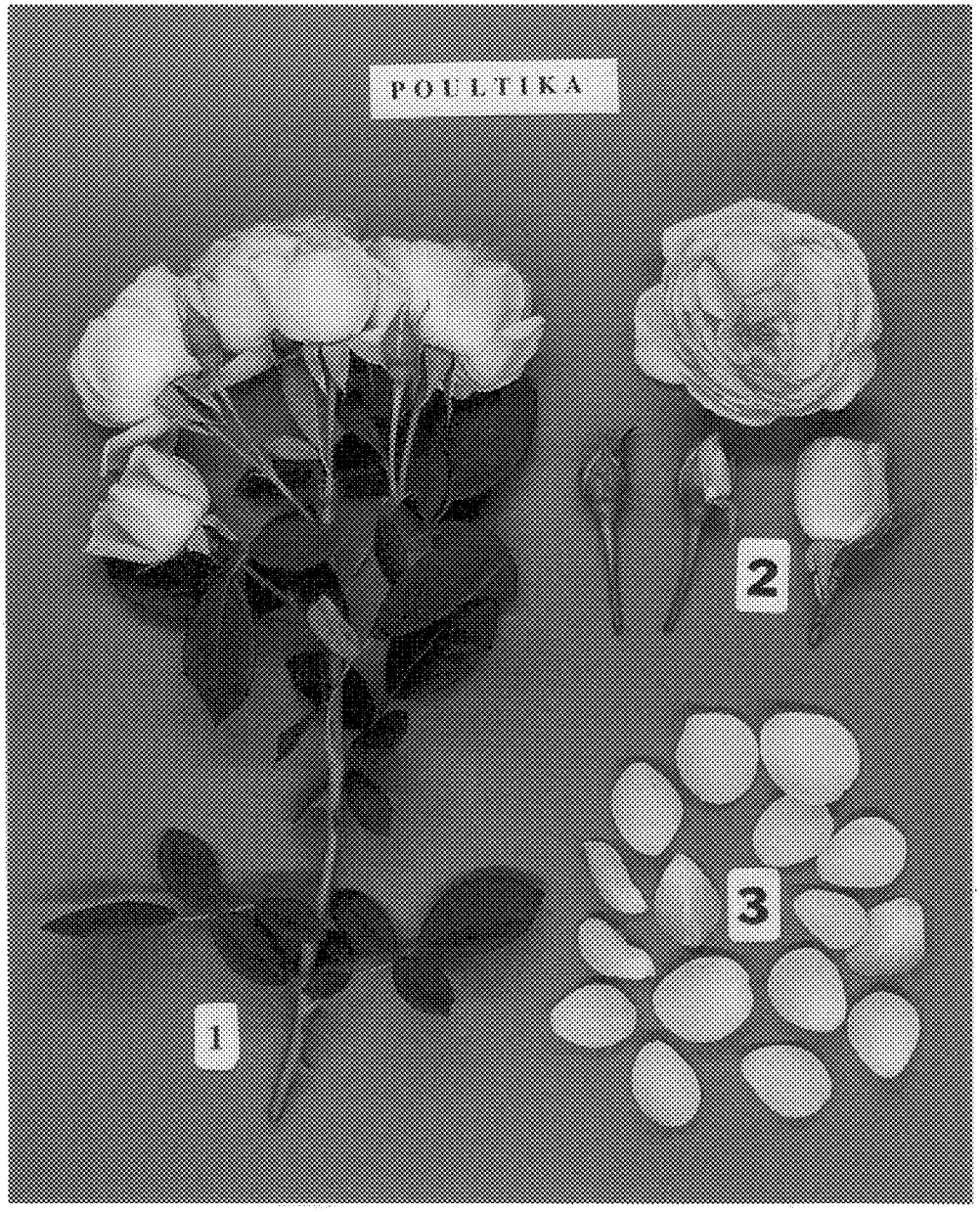
POULTIKA
1
2
3

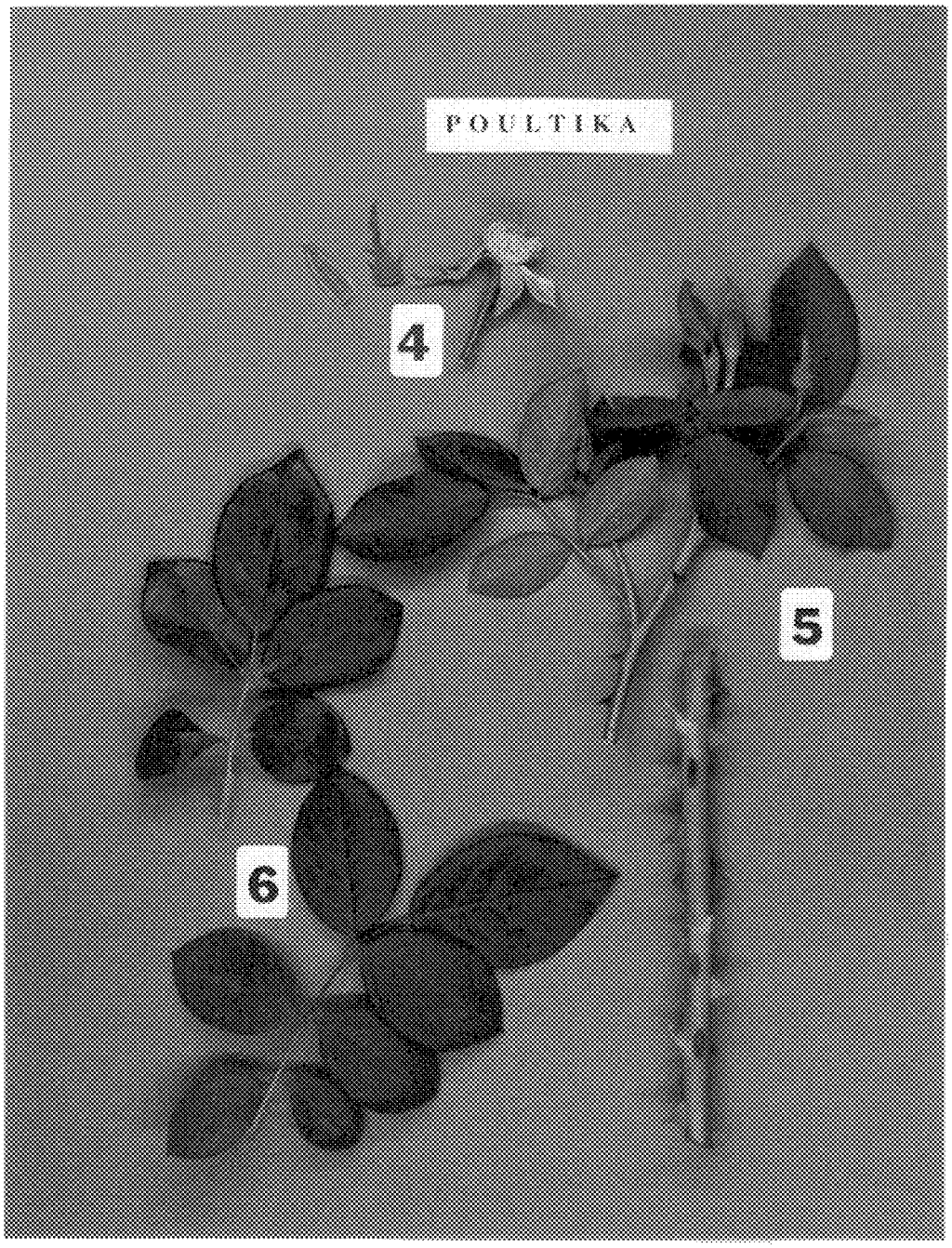
POULTIKA
4
5
6